United States Patent
Kim et al.

(10) Patent No.: US 9,696,301 B2
(45) Date of Patent: Jul. 4, 2017

(54) METHOD FOR SEPARATING NANOPARTICLES AND ANALYZING BIOLOGICAL SUBSTANCE USING MICROFLUIDIC CHIP

(71) Applicant: SNU R&DB FOUNDATION, Seoul (KR)

(72) Inventors: Yong-Kweon Kim, Seoul (KR); Yoon-Sik Lee, Gyeonggi-do (KR); Yul Koh, Seoul (KR); Homan Kang, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 153 days.

(21) Appl. No.: 14/647,876

(22) PCT Filed: Nov. 20, 2013

(86) PCT No.: PCT/KR2013/010569
§ 371 (c)(1),
(2) Date: May 28, 2015

(87) PCT Pub. No.: WO2014/084545
PCT Pub. Date: Jun. 5, 2014

(65) Prior Publication Data
US 2015/0314291 A1    Nov. 5, 2015

(30) Foreign Application Priority Data
Nov. 28, 2012   (KR) .................. 10-2012-0135918
Nov. 15, 2013   (KR) .................. 10-2013-0139222

(51) Int. Cl.
*B01L 3/00*     (2006.01)
*C23C 16/34*    (2006.01)
(Continued)

(52) U.S. Cl.
CPC .. *G01N 33/54326* (2013.01); *B01L 3/502753* (2013.01); *C23C 16/0245* (2013.01);
(Continued)

(58) Field of Classification Search
CPC ......... B01L 2200/12; B01L 2300/0867; B01L 2300/0874; B01L 2400/043; B01L 2400/086; B01L 3/502753; B01L 2300/0861; C23C 16/0245; C23C 16/345; C23C 16/401; G01N 33/54326; Y10T 436/255

See application file for complete search history.

(56) References Cited

U.S. PATENT DOCUMENTS 5,587,128 A * 12/1996 Wilding ................. B01D 61/18
                                                        216/2
8,182,590 B2   5/2012 Striemer et al.
(Continued)

FOREIGN PATENT DOCUMENTS

JP   2004-267912   9/2004
JP   2008-256701   10/2008
(Continued)

*Primary Examiner* — Jennifer Wecker
(74) *Attorney, Agent, or Firm* — Duane Morris LLP; J. Rodman Steele, Jr.; Gregory M. Lefkowitz

(57) ABSTRACT

The present invention relates to a method for separating nanoparticles and analyzing a biological substance using a microfluidic chip. The microfluidic chip of the present invention is effective in more sensitively and precisely detecting an analyte. According to the present invention, the use of the microfluidic chip enables the separation of nanoparticles through separation holes on the basis of size, achieving highly reliable analysis of a biological substance. In conclusion, the microfluidic chip of the present invention uses separation holes adapted to the size of nanoparticles to greatly increase the reliability of analysis of a biological substance, which will contribute to a marked improvement in the reliability of analysis based on microfluidics and a microfluidic system.

20 Claims, 14 Drawing Sheets

(51) Int. Cl.
*C23C 16/40* (2006.01)
*C23C 16/02* (2006.01)
*G01N 33/543* (2006.01)

(52) U.S. Cl.
CPC .......... *C23C 16/345* (2013.01); *C23C 16/401* (2013.01); *B01L 2200/12* (2013.01); *B01L 2300/0867* (2013.01); *B01L 2300/0874* (2013.01); *B01L 2400/043* (2013.01); *B01L 2400/086* (2013.01); *Y10T 436/255* (2015.01)

(56) References Cited

U.S. PATENT DOCUMENTS

| | | | |
|---|---|---|---|
| 8,501,668 B2 | 8/2013 | McGrath et al. | |
| 8,518,276 B2 | 8/2013 | Striemer et al. | |
| 2004/0051154 A1* | 3/2004 | Yamakawa | B01L 3/50255 257/414 |
| 2004/0161369 A1* | 8/2004 | Chan | B01D 67/0062 422/82.05 |
| 2011/0171724 A1* | 7/2011 | Sheldon | C12M 41/14 435/297.1 |
| 2014/0008210 A1* | 1/2014 | Guia | G01N 1/34 204/158.21 |
| 2014/0271245 A1* | 9/2014 | Harper | F16K 15/144 417/53 |
| 2014/0342441 A1* | 11/2014 | Yu | G01N 33/50 435/287.2 |

FOREIGN PATENT DOCUMENTS

KR 1020090110102 10/2009
KR 1020120056442 6/2012

\* cited by examiner

METHOD FOR SEPARATING NANOPARTICLES AND ANALYZING BIOLOGICAL SUBSTANCE USING MICROFLUIDIC CHIP

CROSS-REFERENCE TO RELATED APPLICATIONS

This application is a §371 national stage entry of International Application No. PCT/KR2013/010569, filed Nov. 20, 2013, which claims priority to South Korean Patent Application No. 10-2012-0135918 filed Nov. 28, 2012 and South Korean Patent Application No. 10-2013-0139222 filed Nov. 15, 2013, the entire contents of which are incorporated herein by reference.

TECHNICAL FIELD

The present invention relates to a method for separating nanoparticles and analyzing a biological substance using a microfluidic chip. More specifically, the present invention relates to a method for separating nanoparticles and analyzing a biological substance as an analyte based on the use of a microfluidic chip that more sensitively and reliably detects the analyte.

BACKGROUND ART

Since the completion of the Human Genome Project and the beginning of the post-genome era, much biological information has emerged that is difficult to quickly process with existing laboratory analysis systems. Under such circumstances, vital phenomena have been investigated, new drugs have been developed, and progress in the development of biological detection systems for diagnosis has been made based on microfluidics.

The performance of microfluidic chips, such as labs-on-a-chip, based on microfluidics is determined by the ability of the microfluidic chips to accurately and conveniently analyze samples in a short time using smaller amounts of the microfluidic chips. Much research is currently being conducted in various fields to develop microfluidic chips with higher performance.

However, such microfluidic chips suffer from difficulty in sensitively detecting micro- or nano-sized samples and reaction products, do not effectively filter materials remaining unreacted therein, and fail to provide highly sensitive and reliable analysis results because the reaction products and unreacted reactants coexist.

DETAILED DESCRIPTION OF THE INVENTION

Problems to be Solved by the Invention

The present invention has been made in an effort to solve the above problems, and it is an object of the present invention to provide a microfluidic chip that detects an analyte in a more sensitive and precise manner to draw highly reliable analysis results and a method for analyzing a biological substance using the microfluidic chip. It is a particular object of the present invention to provide a highly reliable microfluidic chip that can separate nanoparticles through nano-sized holes on the basis of size and a method for analyzing a biological substance using the microfluidic chip.

Means for Solving the Problems

One aspect of the present invention provides a microfluidic chip including a sample inlet, a fluid inlet, and a fluidic channel wherein the fluidic channel consists of a reaction zone, a separation zone, and a discharge zone sequentially disposed in the downstream direction and the separation zone includes a separation membrane formed with one or more separation holes through which nanoparticles pass.

The separation zone of the fluidic channel has concave grooves formed in the lower layer of the fluidic channel and covered with the separation membrane.

The upper surface of the separation membrane is in contact with a barrier extending from the upper layer of the fluidic channel.

The barrier is in contact with a middle portion between the front end of the separation membrane toward the inlets and the rear end of the separation membrane toward the discharge zone.

The separation holes are from 100 nm to 1000 nm in size.

The separation membrane is produced by sequentially forming a silicon nitride film and a silicon oxide film on the surface of a substrate.

A silicon oxide film is formed on the surface of the separation holes.

A magnetic force application unit is provided between the reaction zone and the separation zone of the fluidic channel.

An outlet is disposed between the magnetic force application unit and the separation zone to discharge unreacted samples therethrough.

A further aspect of the present invention provides a method for detecting a biological substance using the microfluidic chip, including 1) introducing samples and a fluid into the fluidic channel of the microfluidic chip, 2) allowing the samples to react in the reaction zone to produce reaction products, 3) detecting the reaction products not passing through the separation holes present in the separation zone of the fluidic channel, and 4) analyzing the detected reaction products.

In step 1), magnetic nanoparticles, a biological substance, and a probe are introduced as the samples. In step 2), the samples are allowed to react to form magnetic nanoparticles-biological substance-probe complexes.

A receptor bound to the magnetic nanoparticles and a receptor bound to the probe recognize the biological substance to form the magnetic nanoparticles-biological substance-probe complexes.

The method further includes fixing and collecting unreacted magnetic nanoparticles and the magnetic nanoparticles-biological substance-probe complexes by the magnetic force application unit between steps 2) and 3).

The method further includes discharging unreacted samples unfixed by the magnetic force application unit through the outlet after the fixing/collection step.

After discharge of the unreacted samples, the application of the magnetic force by the magnetic force application unit is stopped to allow the unreacted magnetic nanoparticles and the magnetic nanoparticles-biological substance-probe complexes to move in the direction from the inlets of the fluidic channel toward the discharge zone.

After movement of the unreacted magnetic nanoparticles and the magnetic nanoparticles-biological substance-probe complexes toward the discharge zone, the unreacted magnetic nanoparticles pass through the separation holes but the magnetic nanoparticles-biological substance-probe complexes do not pass through the separation holes.

Another aspect of the present invention provides a method for producing a separation membrane for the microfluidic chip, including 1) forming a silicon nitride film on a silicon substrate or a substrate including silicon by chemical vapor deposition (CVD), 2) forming 2 to 3 μm-sized separation holes in the substrate, and 3) forming a silicon oxide film on the substrate including the separation holes by chemical vapor deposition (CVD).

In step 3), the chemical vapor deposition (CVD) is continued until the size of the separation holes is reduced to 100 nm to 1000 nm.

Effects of the Invention

The microfluidic chip of the present invention is effective in more sensitively and precisely detecting an analyte. According to the present invention, the use of the microfluidic chip enables the separation of nanoparticles through separation holes on the basis of size, achieving highly reliable analysis of a biological substance. In conclusion, the microfluidic chip of the present invention uses separation holes adapted to the size of nanoparticles to greatly increase the reliability of analysis of a biological substance, which will contribute to a marked improvement in the reliability of analysis based on microfluidics and a microfluidic system.

BEST MODE FOR CARRYING OUT THE INVENTION

Figure 1:
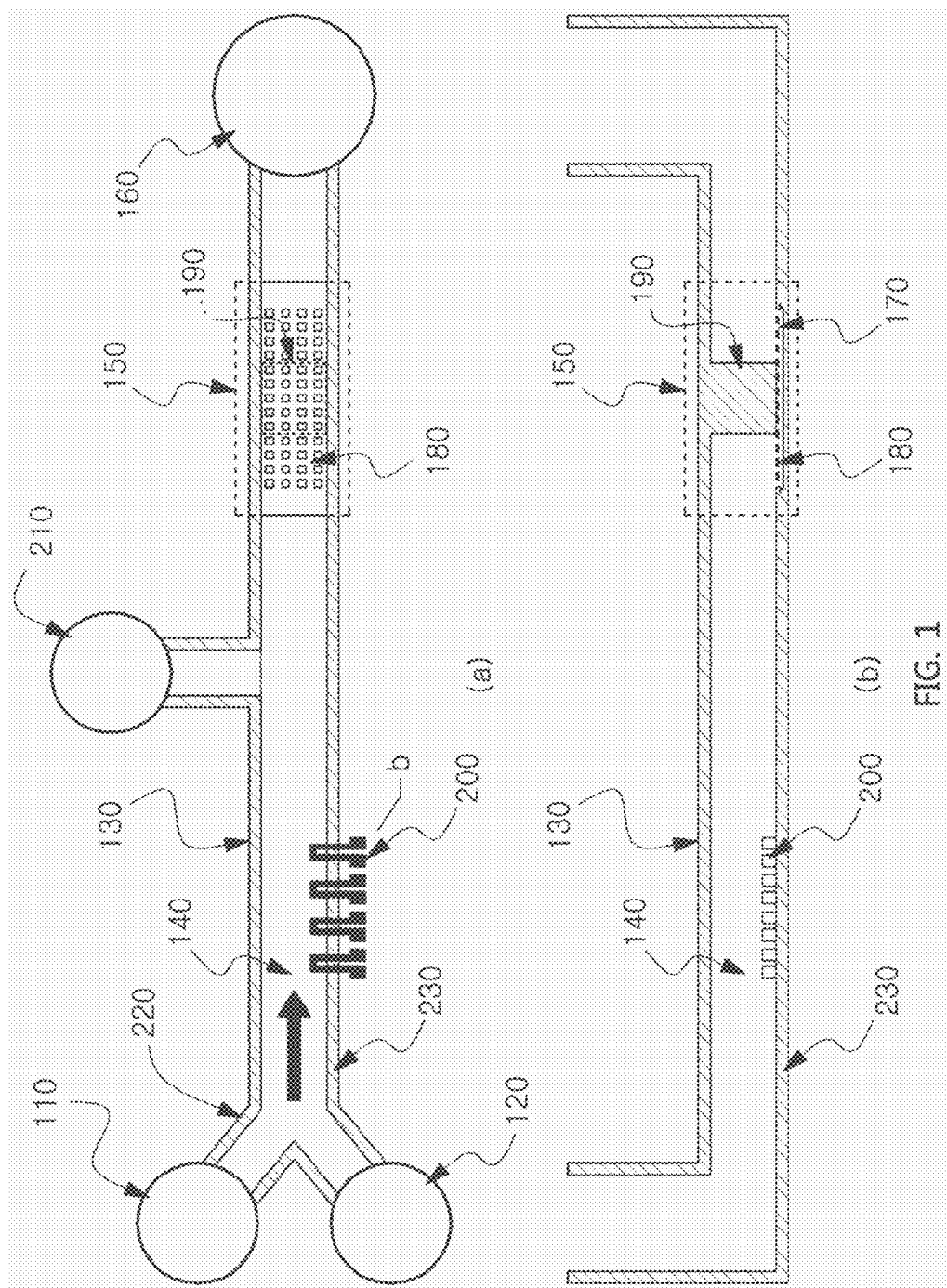
FIG. 1 shows (a) a plan view and (b) a cross-sectional view illustrating the constitution of a microfluidic chip fabricated in Example 1.

Thus, the present inventors have earnestly and intensively conducted research to develop a microfluidic chip capable of providing highly reliable analysis results. As a result, the present inventors have found a microfluidic chip and a method for analyzing a biological substance using the microfluidic chip according to the present invention.

Specifically, the microfluidic chip of the present invention includes a sample inlet 110, a fluid inlet 120, and a fluidic channel 130. The fluidic channel consists of a reaction zone 140, a separation zone 150, and a discharge zone 160 sequentially disposed in the downstream direction and the separation zone 150 may include a separation membrane 180 formed with one or more separation holes 170 through which nanoparticles pass.

Generally, the ability of the microfluidic chip to sensitively and accurately detect reaction products is a very important factor determining the reliability of analysis of the reaction products by the microfluidic chip. The microfluidic chip of the present invention enables a more sensitive and accurate analysis by the separation membrane 180 including the separation holes 170.

Preferably, the separation zone 150 of the fluidic channel 130 has concave grooves formed in a lower layer 230 of the fluidic channel 130. The concave grooves may be covered with the separation membrane 180.

The upper surface of the separation membrane is preferably in contact with a barrier 190 extending from an upper layer 220 of the fluidic channel 130.

The barrier 190 may be in contact with a middle portion between the front end of the separation membrane 180 toward the inlets 110 and 120 and the rear end of the separation membrane 180 toward the discharge zone 160.

Preferably, reaction products of samples are separated from unreacted samples in the separation zone 150 of the fluidic channel. The unreacted samples are preferably magnetic nanoparticles (MNPs).

The separation of the reaction products from the unreacted samples in the separation zone can be performed through the separation holes 170 of the separation membrane 180.

The separation holes of the separation membrane 180 are not limited to a particular size so long as they are large enough to pass the unreacted magnetic nanoparticles (MNPs) therethrough but preferably have a diameter of 100 nm to 1000 nm. If the diameter of the separation holes is smaller than 100 nm, a smooth flow of the fluid is not ensured and the unreacted magnetic nanoparticles do not easily pass through the separation holes.

Meanwhile, if the size of the separation holes exceeds 1000 nm, the reaction products of the samples as well as the unreacted magnetic nanoparticles may pass through the separation holes.

The morphology and structure of the separation holes are not particularly limited so long as the nanoparticles can pass through the separation holes and the reaction products can be separated by the separation holes. Preferably, the separation holes are circular in shape. Alternatively, the separation holes may be thin, long, rectangular nanoslits.

The separation membrane is not particularly limited but is preferably one in which a plurality of linear groups of the separation holes are arranged in a zigzag configuration. This arrangement allows the formation of the separation holes with a smaller diameter during production of the separation membrane, enabling a more precise separation of the nanoparticles.

The separation membrane 180 is not particularly limited so long as it can pass the magnetic nanoparticles therethrough without hindering the flow of the fluid in the fluidic channel 130. Preferably, the separation membrane 180 uses a silicon substrate or a substrate including silicon.

Preferably, the separation membrane is produced by forming a silicon nitride film and a silicon oxide film on the surface of the silicon substrate or substrate including silicon by chemical vapor deposition (CVD). More preferably, the silicon nitride film and the silicon oxide film are sequentially formed on the surface of the substrate.

A silicon oxide film is preferably formed on the surface of the separation holes 170 by chemical vapor deposition (CVD).

The size of the separation holes may be adjusted in the range of 100 nm to 1000 nm by chemical vapor deposition. The separation holes are formed so as to have a smaller size than the nanoparticle complexes and a larger size than the magnetic nanoparticles. As a result, the relatively small magnetic nanoparticles pass through the separation holes so that the relatively large nanoparticle complexes can be selectively separated.

Any polymeric material that does not hinder the flow of the fluid may be used without particular limitation for the fluidic channel 130. The polymeric material is preferably selected from the group consisting of polydimethylsiloxane (PMDS), polymethylmethacrylate (PMMA), polycarbonate, polycyclic olefin, polyimide, polyurethane, and mixtures thereof. The portion of the lower layer 230 of the fluidic channel located in the separation zone 150 may be formed using silicon, glass or a mixture thereof with the polymeric material.

Reactants and any material necessary for the reaction of the reactants may be introduced into the sample inlet 110 without particular limitation but are preferably selected from the group consisting of magnetic nanoparticles, biological substances, probes, and mixtures thereof. The biological substances are preferably antibodies or biomarkers.

Samples may pre-react before introduction through the inlet 110. Preferably, the samples react in the reaction zone 140.

The reaction products produced in the reaction zone 140 are preferably magnetic nanoparticles-biological substance-probe complexes. A receptor bound to the magnetic nanoparticles and a receptor bound to the probe recognize the biological substance to form the magnetic nanoparticles-biological substance-probe complexes.

A magnetic force application unit 200 is preferably provided between the reaction zone 140 and the separation zone 150 of the fluidic channel.

Preferably, the magnetic force application unit 200 collects unreacted magnetic nanoparticles and the magnetic nanoparticles-biological substance-probe complexes by the application of a magnetic force.

An outlet 210 may be disposed between the magnetic force application unit 200 and the separation zone 150 to discharge unreacted samples therethrough.

The flow of the fluid for discharging the unreacted samples is preferably controlled using a microvalve, such as a pneumatic valve.

After discharge of the unreacted samples through the outlet 210, the application of the magnetic force by the magnetic force application unit is stopped. As a result, the unreacted magnetic nanoparticles and the magnetic nanoparticles-biological substance-probe complexes collected by the magnetic force application unit 200 can be moved to the separation zone 150 along the fluidic channel 130.

The unreacted magnetic nanoparticles and the magnetic nanoparticles-biological substance-probe complexes can be separated by the separation membrane 180. Preferably, the unreacted magnetic nanoparticles smaller than the separation holes of the separation membrane 180 passes through the separation holes 170 but the magnetic nanoparticles-biological substance-probe complexes larger than the separation holes do not pass through the separation holes, That is, the unreacted magnetic nanoparticles and the magnetic nanoparticles-biological substance-probe complexes can be selectively separated through the separation holes on the basis of size.

Thus, the high-purity magnetic nanoparticles-biological substance-probe complexes can be detected by the separation membrane 180 including the separation holes.

Therefore, the use of the microfluidic chip according to the present invention allows for the detection of the high-purity magnetic nanoparticles-biological substance-probe complexes, achieving a more accurate, sensitive, and reliable analysis of the biological substance.

In a further aspect, the present invention provides a method for detecting a biological substance using the microfluidic chip. Specifically, the method includes 1) introducing samples and a fluid into the fluidic channel of the microfluidic chip, 2) allowing the samples to react in the reaction zone to produce reaction products, 3) detecting the reaction products not passing through the separation holes present in the separation zone of the fluidic channel, and 4) analyzing the detected reaction products.

The samples are not particularly limited so long as they can react in the microfluidic chip to detect a biological substance. Preferably, the samples are magnetic nanoparticles, a biological substance, and a probe. Preferably, the magnetic nanoparticles, the biological substance, and the probe react to form magnetic nanoparticles-biological substance-probe complexes.

A receptor bound to the magnetic nanoparticles and a receptor bound to the probe recognize the biological substance to form the magnetic nanoparticles-biological substance-probe complexes.

The magnetic nanoparticles-biological substance-probe complexes can be detected because the complexes do not pass through the separation holes present in the separation zone of the fluidic channel due to their larger size than the separation holes.

Preferably, the method further includes fixing and collecting the magnetic nanoparticles-biological substance-probe complexes by the magnetic force application unit between steps 2) and 3).

When a magnetic force is applied by the magnetic force application unit, the unreacted magnetic nanoparticles and the magnetic nanoparticles-biological substance-probe complexes can be fixed by the attractive force between the magnetic nanoparticles and the magnetic force.

This fixing allows unreacted samples except the unreacted magnetic nanoparticles and the magnetic nanoparticles-biological substance-probe complexes to move through the fluidic channel.

Preferably, the method further includes discharging the unreacted samples unfixed by the magnetic force application unit through the outlet. When the unreacted samples are discharged through the outlet, the higher purity magnetic nanoparticles-biological substance-probe complexes are preferably detected, achieving high analysis reliability.

After the unreacted samples are discharged through the outlet, the application of the magnetic force is preferably stopped to allow the unreacted magnetic nanoparticles and the magnetic nanoparticles-biological substance-probe complexes to move toward the discharge zone of the fluidic channel.

The unreacted magnetic nanoparticles and the magnetic nanoparticles-biological substance-probe complexes reach the separation zone, where they can be separated by the separation membrane including the separation holes. At this time, the unreacted magnetic nanoparticles smaller than the separation holes can pass through the separation holes but the magnetic nanoparticles-biological substance-probe complexes larger than the separation holes cannot pass through the separation holes. That is, the magnetic nanoparticles-biological substance-probe complexes can be selectively separated by the separation holes based on the size difference between the unreacted magnetic nanoparticles and the magnetic nanoparticles-biological substance-probe complexes.

The size of the separation holes may be from 100 nm to 1000 nm. The size of the magnetic nanoparticles is preferably smaller than that of the separation holes, more preferably from 30 to 500 nm. The size of the magnetic nanoparticles-biological substance-probe complexes is preferably larger than that of the separation holes, more preferably from 200 to 1500 nm. Therefore, the magnetic nanoparticles smaller than the separation holes can easily pass through the separation holes but the magnetic nanoparticles-biological substance-probe complexes larger than the separation holes cannot pass through the separation holes.

As a consequence, the separation membrane including the separation holes can separate the high-purity magnetic nanoparticles-biological substance-probe complexes, enabling a more accurate analysis of the biological substance.

The detected magnetic nanoparticles-biological substance-probe complexes, which have not passed through the separation holes, can be used for the analysis of the biological substance. The biological substance may be analyzed by any method known in the art, preferably Raman spectroscopy.

In another aspect, the present invention provides a method for producing a separation membrane including separation holes for the microfluidic chip. Specifically, the method includes 1) forming a silicon nitride film on a silicon substrate or a substrate including silicon by chemical vapor deposition (CVD), 2) forming 2 to 3 µm-sized separation holes in the substrate, and 3) forming a silicon oxide film on the substrate including the separation holes by chemical vapor deposition (CVD).

In step 3), the chemical vapor deposition (CVD) for the formation of the silicon oxide film is continued until the size of the separation holes is reduced to 100 nm to 1000 nm. If the size of the separation holes is less than 100 nm, unreacted magnetic nanoparticles do not effectively pass through the separation holes. Meanwhile, if the size of the separation holes exceeds 1000 nm, magnetic nanoparticles-biological substance-probe complexes may pass through the separation holes.

Mode for Carrying Out the Invention

The present invention will be explained in detail in such a manner that those with ordinary knowledge in the art can easily carry out the invention with reference to the following examples. The invention may, however, be embodied in many different forms and should not be construed as limited to the exemplary embodiments set forth herein.

EXAMPLES

Example 1: Fabrication of Micofluidic Chip with 250 nm-Sized Separation Holes

In this example, a microfluidic chip having a sample inlet, a fluid inlet, a fluidic channel, a reaction zone, a separation zone, and a discharge zone was fabricated. Separation holes through which nanoparticles can pass were located at the lower side of the fluidic channel. The separation holes were formed by the following procedure. First, a silicon nitride film was formed to a thickness of 500 nm-1000 nm on a silicon substrate by chemical vapor deposition (CVD). Micro-sized holes with a 2.5 µm size were patterned on the resulting substrate by photolithography and the silicon nitride film was etched by plasma etching. Thereafter, portions of the silicon substrate exposed by etching of the silicon nitride film were etched to a depth of 3-5 µm by anisotropic etching. Then, additional etching was performed in a TMAH/KOH solution as an etching solution for silicon substrates to form the lower side of the fluidic channel. Finally, a silicon oxide film was formed on the etched silicon substrate by chemical vapor deposition (CVD) to reduce the micro-sized holes (diameter 2.5 µm) to nano-sized separation holes. The thickness of the film was controlled to reduce the diameter of the separation holes to 250 nm.

The upper side of the fluidic channel was formed by molding of polydimethylsiloxane (PDMS). The lower side of the fluidic channel and the separation holes were oxidized by treatment with oxygen plasma and a barrier was formed to connect both sides of the fluidic channel. A magnetic force application unit and an outlet through which unreacted reactants can be discharged were provided, completing the fabrication of the microfluidic chip.

FIG. 1 shows (a) a plan view and (b) a cross-sectional view illustrating constitution of the microfluidic chip fabricated in Example 1.

Figure 2:
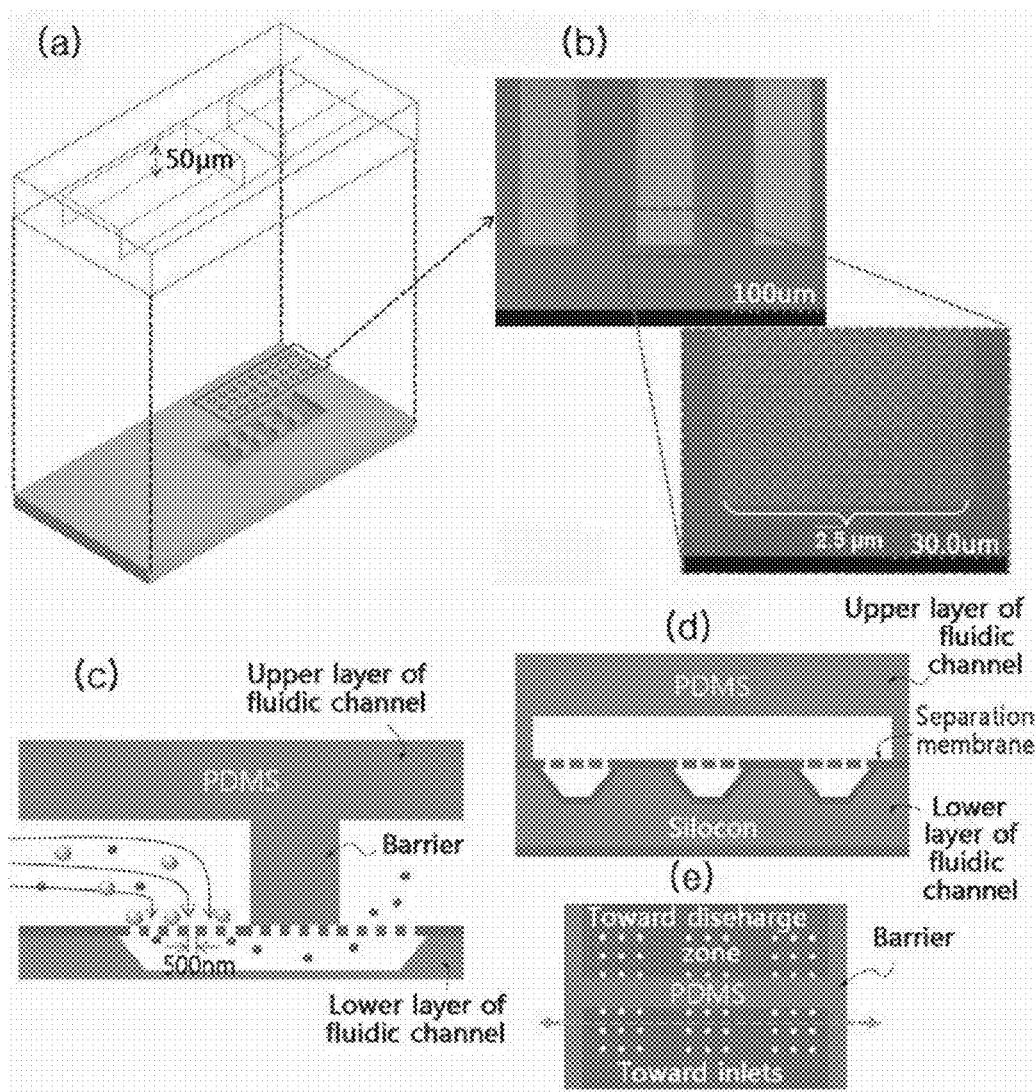
FIG. 2 shows the periphery of separation holes of a microfluidic chip fabricated in Example 1 and a scanning electron microscopy (SEM) image of the separation holes before the formation of a silicon oxide film.

FIG. 2 shows enlarged diagrams of the periphery of the separation holes of the microfluidic chip fabricated in Example 1. As shown in FIG. 2, the separation holes are located opposite the upper PDMS side of the fluidic channel. FIG. 2 shows (a) a three-dimensional diagram to specifically illustrate the locations of the separation holes spaced apart from each other and (b) a scanning electron microscopy image showing the arrangement of the 2.5 µm-sized separation holes on the substrate before formation of the silicon oxide film after etching of the silicon nitride film. (c) of FIG. 2 also shows the principle that small nanoparticles pass through the separation holes. FIG. 2 also shows (d) longitudinal and (e) transverse cross-sectional diagrams of the microfluidic chip in which the separation holes are grouped.

Figure 3:
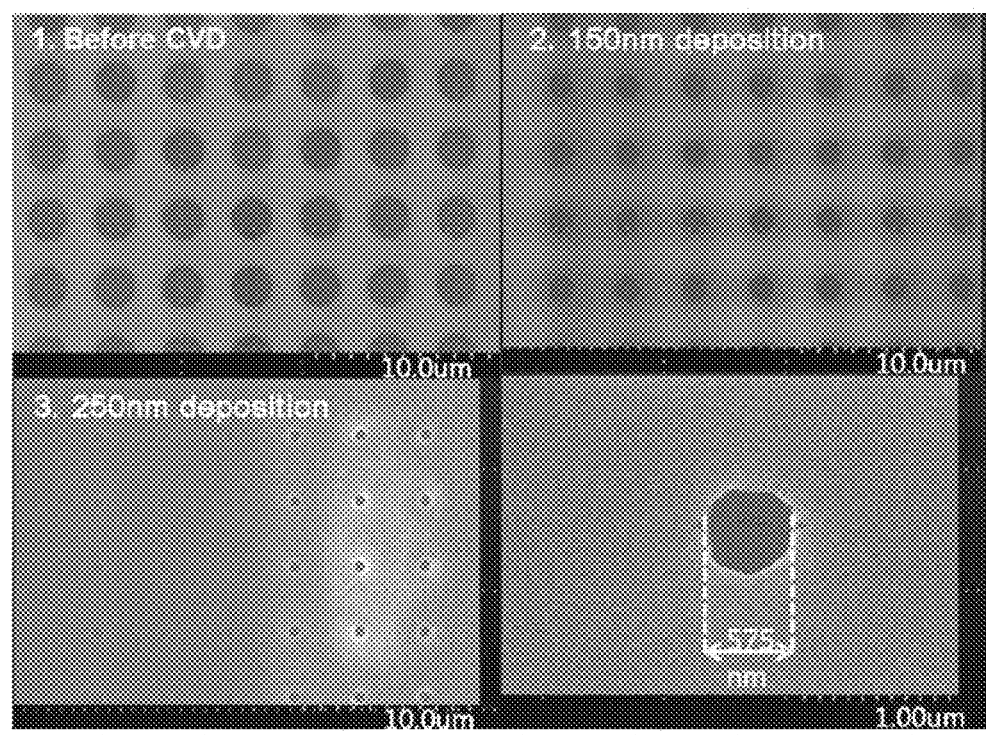
FIG. 3 shows scanning electron microscopy (SEM) images showing changes in the size of separation holes with increasing thickness of a film formed by chemical vapor deposition in Example 1.

FIG. 3 shows scanning electron microscopy images showing a profile in which the size (2.5 µm) of the separation holes before deposition of the silicon oxide film after etching of the silicon nitride film was reduced to 575 nm after formation of the silicon oxide film.

Figure 4:
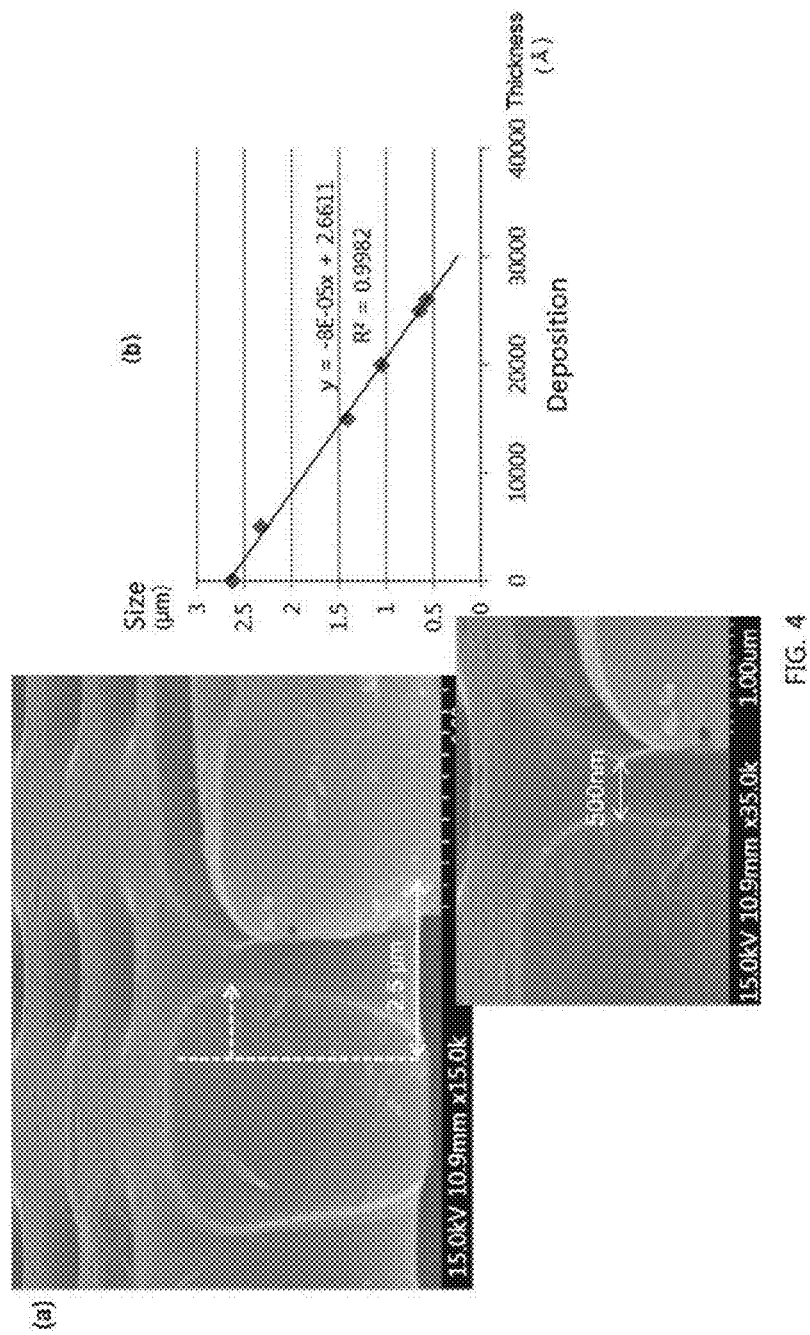
FIG. 4 shows scanning electron microscopy (SEM) images and a graph showing changes in the size of separation holes with increasing thickness of a film formed by chemical vapor deposition in Example 1.

FIG. 4 shows (a) high magnification scanning electron microscope images of the separation holes before and after deposition of the silicon oxide film on the etched silicon substrate and (b) a profile in which the diameter of the separation holes was changed with increasing thickness of the film.

Figure 5:
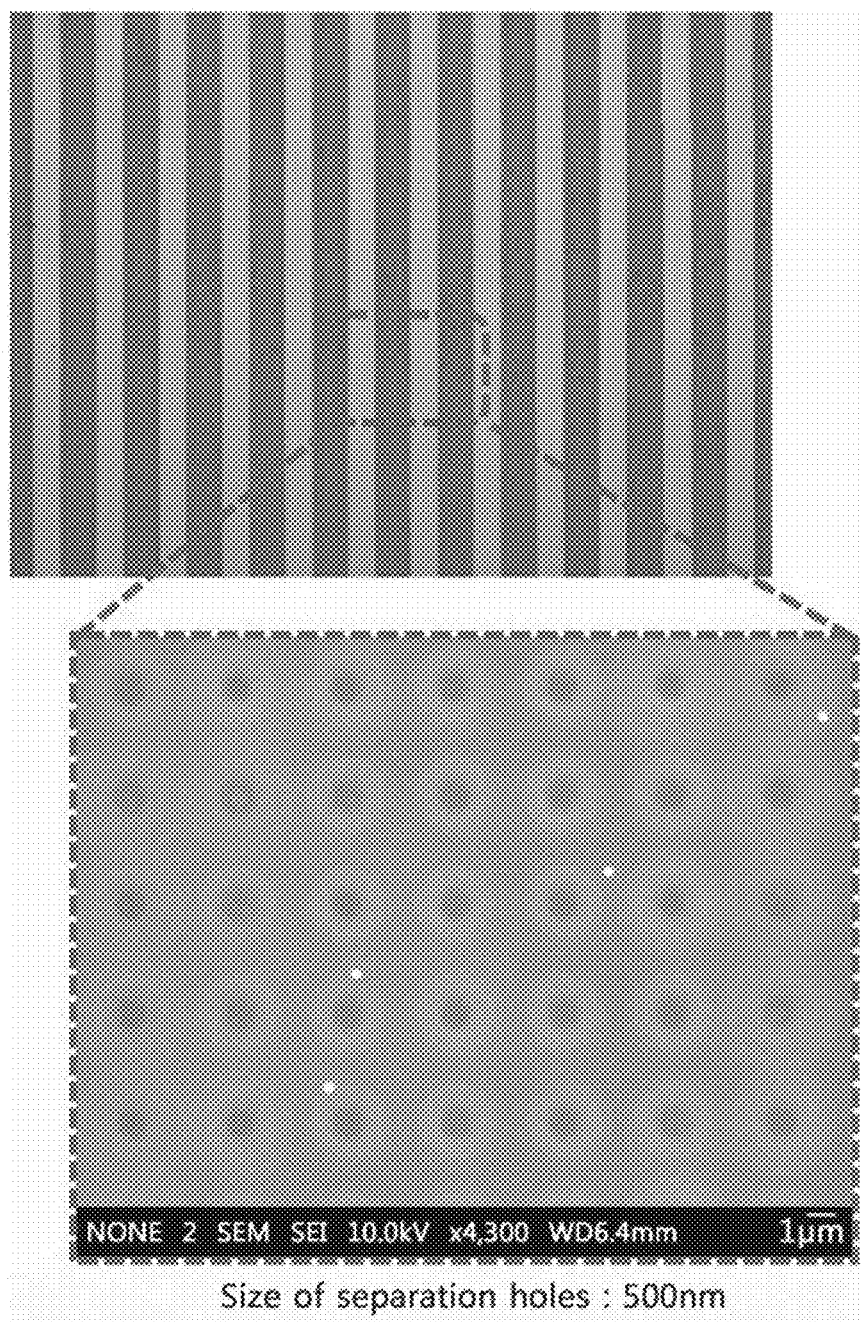
FIG. 5 is an image showing 500 nm-sized separation holes formed in accordance with a preferred embodiment of the present invention.

A microfluidic chip was fabricated in the same manner as in Example 1, except that the size of the separation holes was changed from 250 nm to 500 nm. FIG. 5 is a scanning electron microscopy image of the microfluidic chip. This shows that the size of the holes through which nanoparticles can penetrate can be controlled by chemical vapor deposition. Therefore, the microfluidic chip with the 500 nm-sized holes is also considered a preferred embodiment of the present invention.

Figure 6:
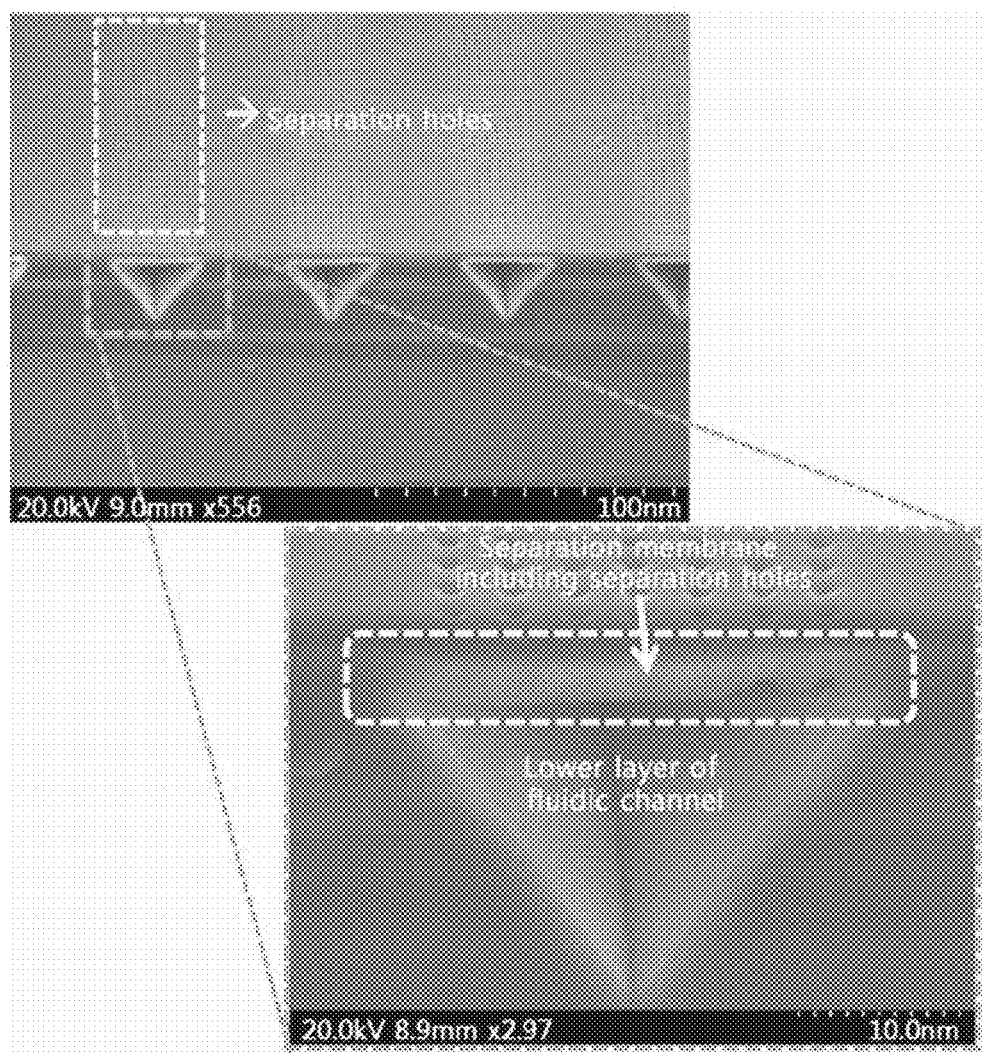
FIG. 6 is a scanning electron microscopy (SEM) image showing a plurality of groups of separation holes formed in a microfluidic chip of the present invention.

FIG. 6 is a scanning electron microscopy (SEM) image showing a plurality of groups of the separation holes formed in the microfluidic chip.

As shown in FIG. 6, the microfluidic chip including the grouped separation holes can more rapidly and efficiently analyze an analyte.

Example 2: Fabrication of Microfluidic Chip Including Separation Membrane Formed with a Plurality of Linear Groups of Separation Holes Arranged in Zigzag Configuration A microfluidic chip was fabricated in the same manner as in Example 1, except that a plurality of linear groups of the separation holes were arranged in a zigzag configuration to produce a separation membrane. At this time, the plasma etching was performed such that the micro-sized holes were arranged in linear groups.

Figure 7:
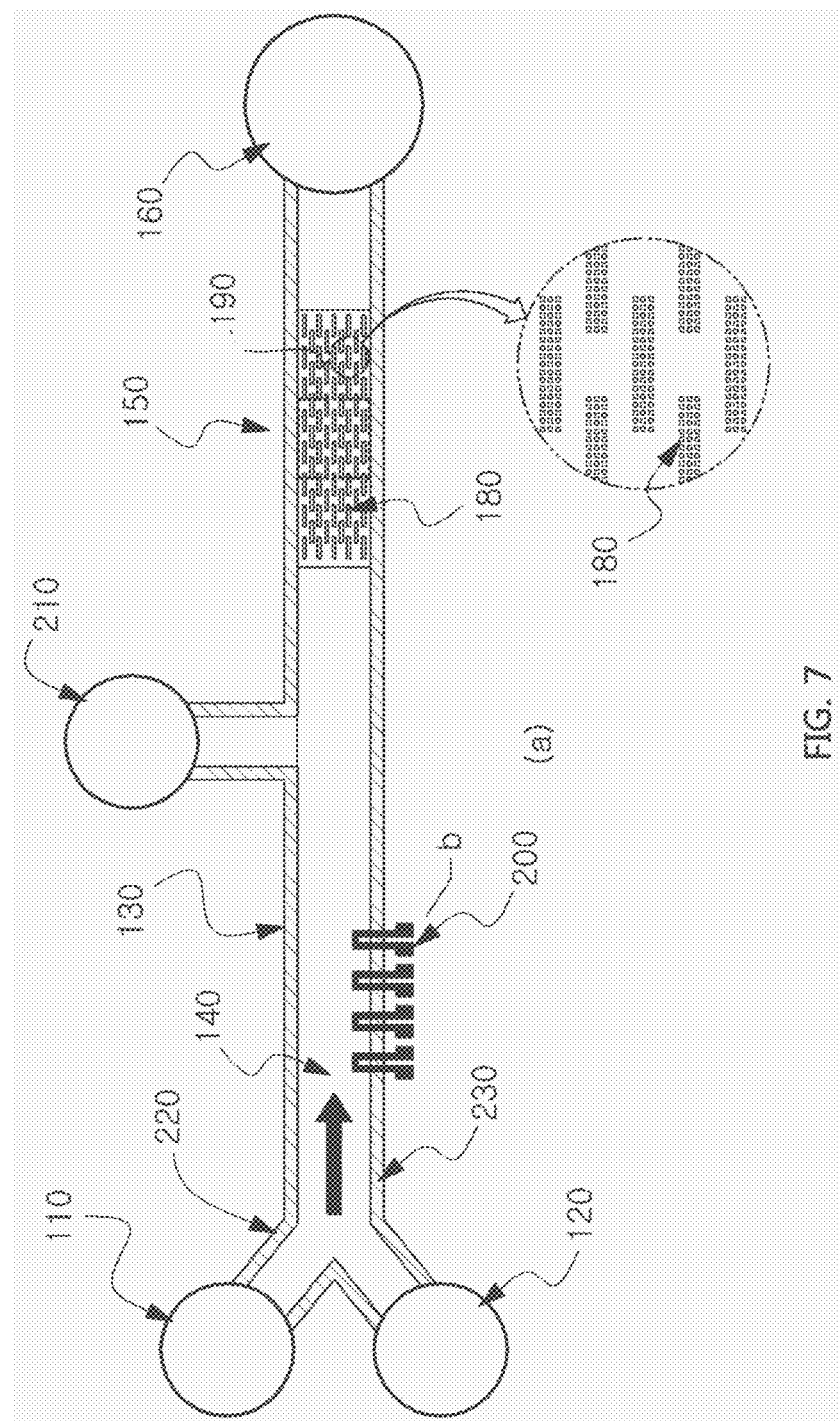
FIG. 7 is a plan view illustrating the constitution of a microfluidic chip fabricated in Example 2.

FIG. 7 is a plan view illustrating the constitution of the microfluidic chip fabricated in Example 2.

Figure 8:
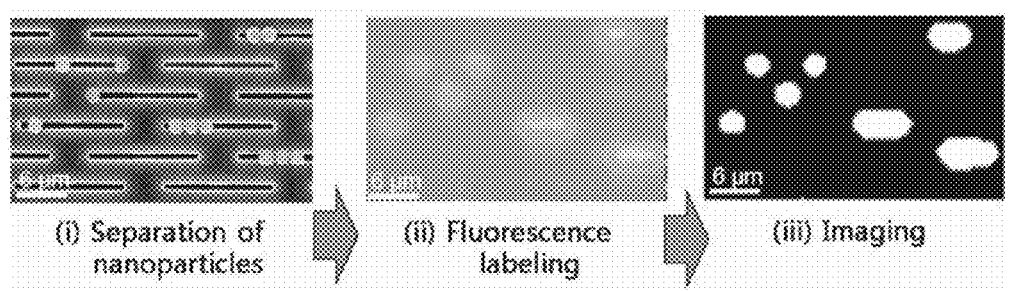
FIG. 8 shows images illustrating the separation of fluorescence-labeled nanoparticles using a microfluidic chip fabricated in Example 2.

FIG. 8 shows images illustrating the separation of fluorescence-labeled nanoparticles using the microfluidic chip fabricated in Example 2.

Figure 9:
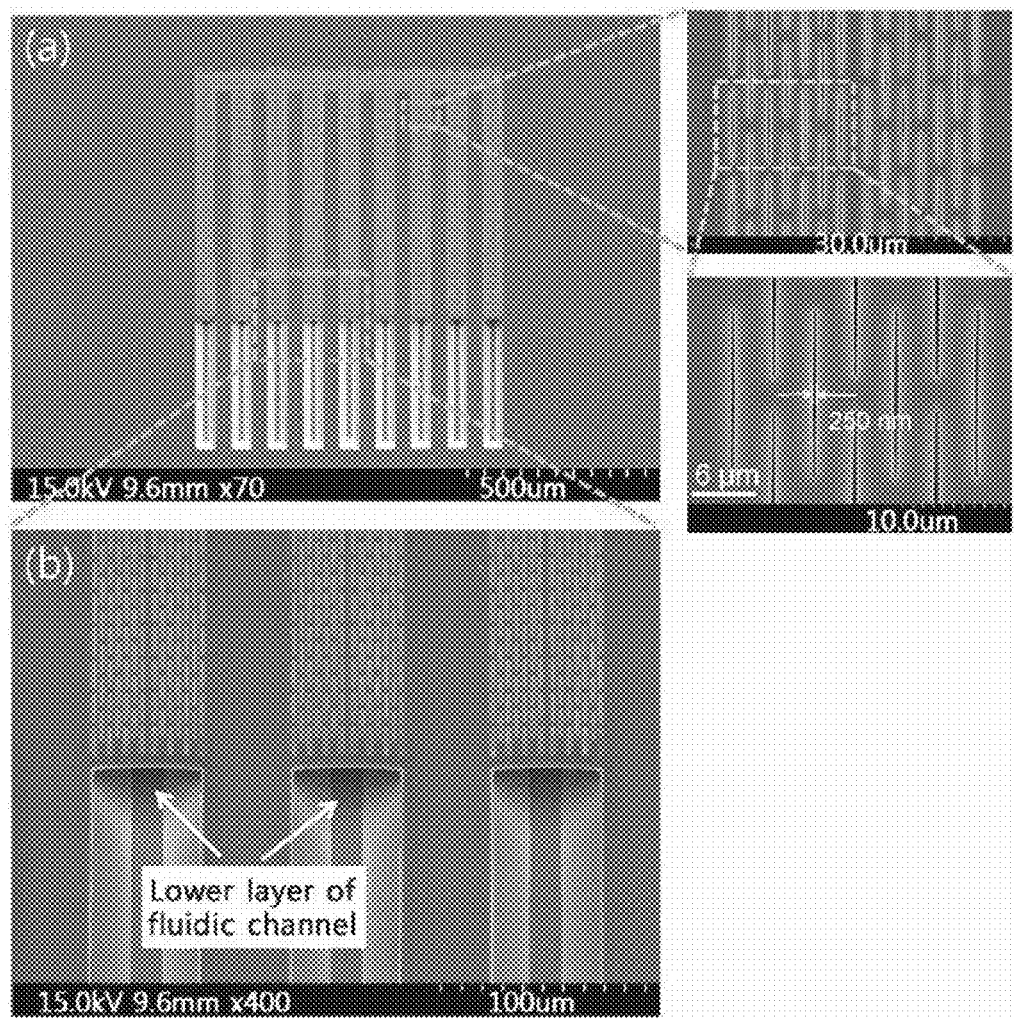
FIG. 9 shows images illustrating a plurality of linear groups of separation holes in a separation membrane of a microfluidic chip fabricated in Example 2.

FIG. 9 shows images illustrating the linear groups of the separation holes in the separation membrane of the microfluidic chip fabricated in Example 2.

Figure 10:
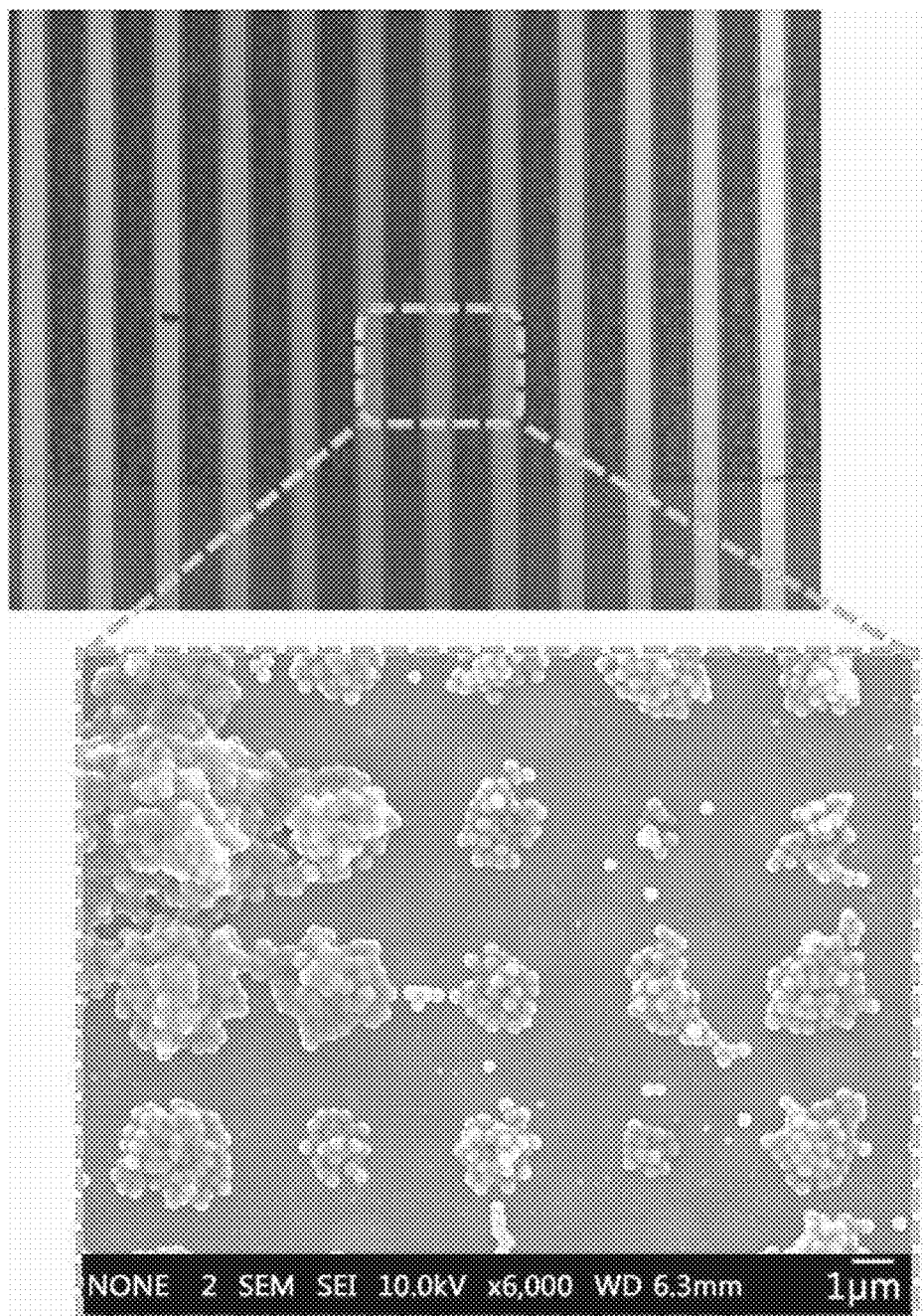
FIG. 10 is a SEM image demonstrating the separation of nanoparticles using a microfluidic chip fabricated in Example 2.

FIG. 10 is a SEM image demonstrating the separation of the nanoparticles using the microfluidic chip fabricated in Example 2.

EXPERIMENTAL EXAMPLES

Experimental Example 1: Selective Separation of Nanoparticles Using the Microfluidic Chips on the Basis of Size 300 nm-sized nanoparticles were allowed to pass through the 250 nm-sized separation holes of the microfluidic chip fabricated in Example 1. An observation was made as to whether or not the nanoparticles passed through the separation holes. The results are shown in FIG. 11.

Figure 11:
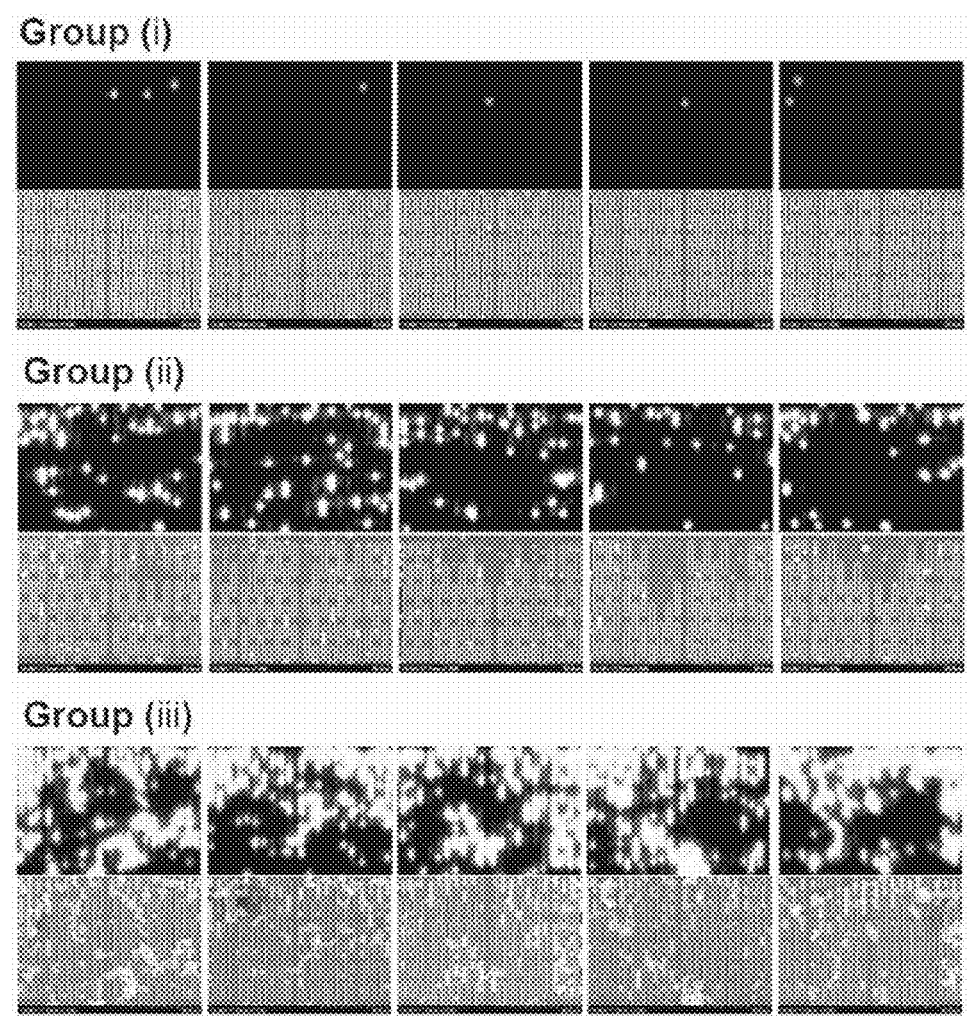
FIG. 11 shows images showing the separation of 300 nm-sized nanoparticles through 250 nm-sized separation holes in a microfluidic chip fabricated in Example 2.

As can be confirmed in FIG. 11, the 300-nm sized nanoparticles failed to pass through the 250-nm sized separation holes and were filtered by the microfluidic chip.

Despite the small size difference (50 nm) between the separation holes and the nanoparticles, the nanoparticles were precisely and sensitively filtered by the microfluidic chip without passing through the separation holes.

These experimental results demonstrate that the microfluidic chip including separation holes whose size is smaller than an analyte enables highly reliable and sensitive analysis of the analyte.

Experimental Example 2: Comparison of Diameters of the Separation Holes of the Microfluidic Chips Fabricated in Examples 1 and 2

Figure 12A:
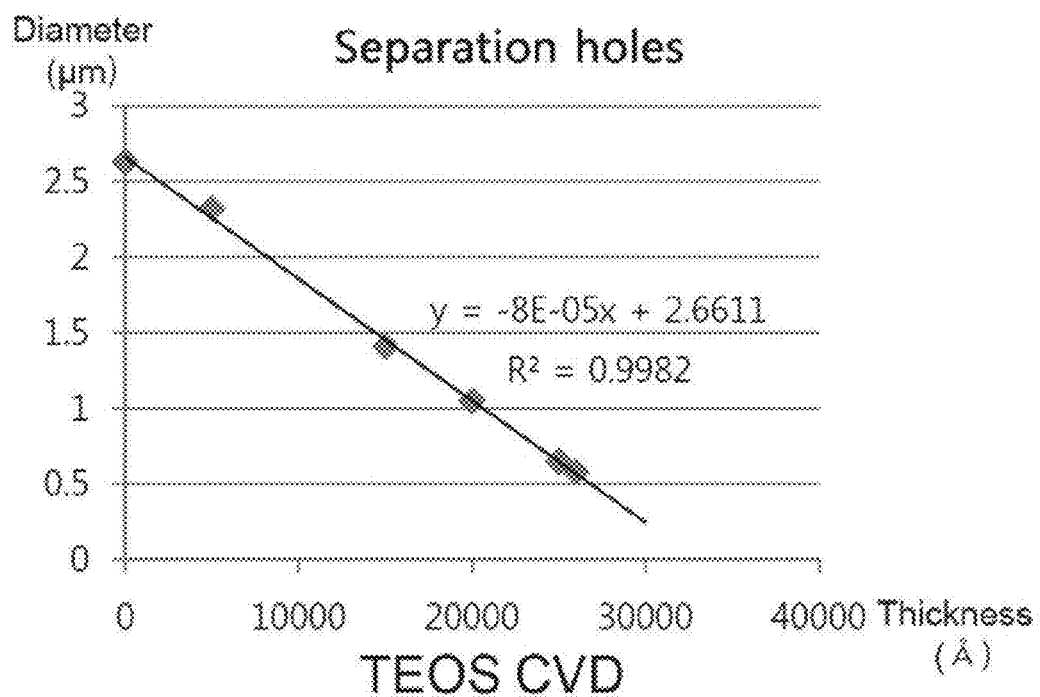
FIGS. 12a and 12b are graphs showing the diameters of separation holes of microfluidic chips fabricated in Examples 1 and 2, respectively.
Figure 12B:
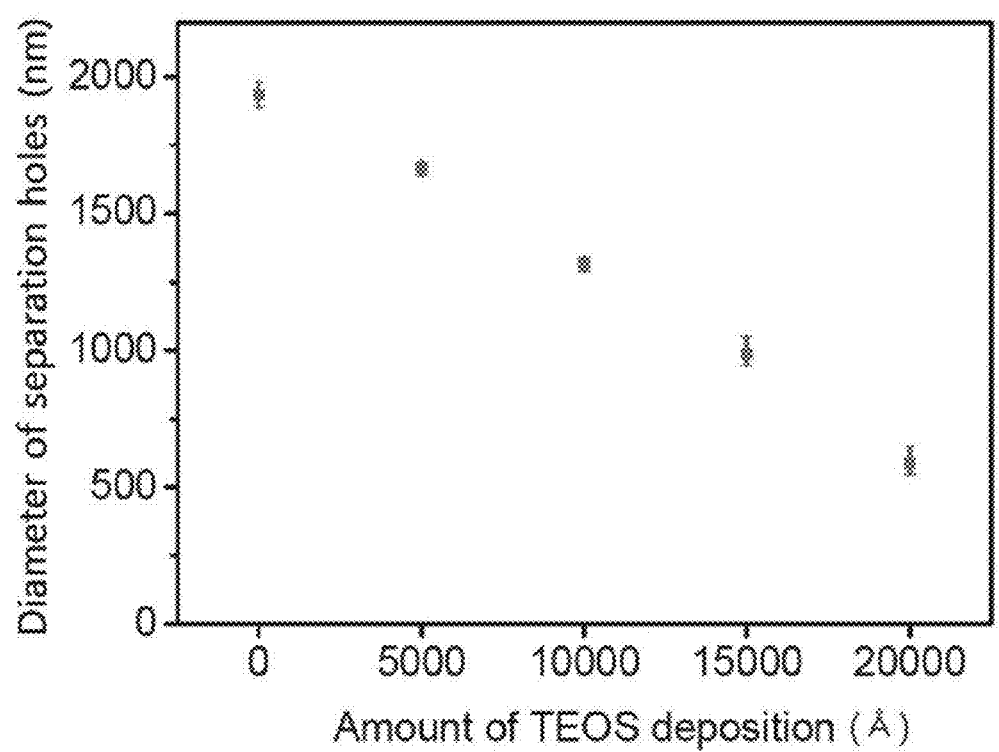

The diameters of the separation holes of the microfluidic chips fabricated in Examples 1 and 2 were measured and are shown in FIG. 12.

As can be seen from FIG. 12, the microfluidic chip of Example 2 (12b) had better ability to precisely separate nanoparticles than that of Example 1 (12a) because the larger amount of the material deposited brought about a marked reduction in the diameter of the separation holes included in the microfluidic chip of Example 2.

Figure 13:
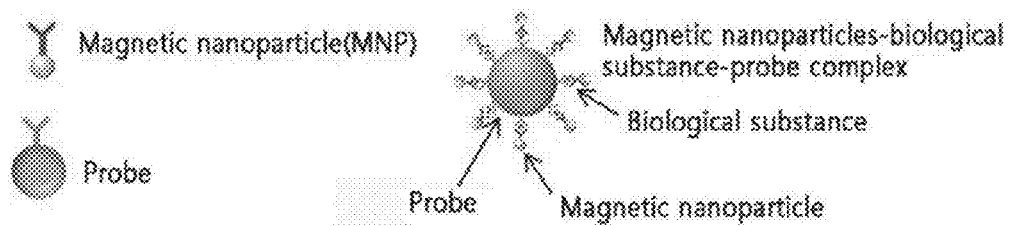
FIG. 13 is a diagram schematically showing magnetic nanoparticles, a probe, and a magnetic nanoparticle-biological substance-probe complex.

FIG. 13 is a diagram schematically showing magnetic nanoparticles as preferred exemplary samples, a probe and a magnetic nanoparticle-biological substance-probe complex.

The results of Experimental Examples 1 and 2 can lead to the conclusion that the microfluidic chips with separation holes enable a more sensitive detection and collection of reaction products to provide highly reliable analysis results.

Although the present invention has been described herein with reference to its preferred embodiments, these embodiments do not serve to limit the invention. It should be understood that various modifications are possible without departing from the scope and spirit of the invention and such modifications are encompassed within the scope of the appended claims.

EXPLANATION OF REFERENCE NUMERALS

110: Sample inlet
120: Fluid inlet
130: Fluidic channel
140: Reaction zone
150: Separation zone
160: Discharge zone
170: Separation holes
180: Separation membrane
190: Barrier
200: Magnetic force application unit
210: Outlet
220: Upper side of the fluidic channel
230: Lower side of the fluidic channel

The invention claimed is:

1. A microfluidic chip comprising a sample inlet, a fluid inlet, and a fluidic channel wherein the fluidic channel consists of a reaction zone, a separation zone, and a discharge zone sequentially disposed in the downstream direction and the separation zone comprises a separation membrane formed with one or more separation holes through which nanoparticles pass,
wherein the separation zone of the fluidic channel has concave grooves formed in the lower layer of the fluidic channel and covered with the separation membrane, and
wherein the upper surface of the separation membrane is in contact with a barrier extending from the upper layer of the fluidic channel.

2. The microfluidic chip according to claim 1, wherein a plurality of linear groups of the separation holes are arranged in a zigzag configuration.

3. The microfluidic chip according to claim 1, wherein the barrier is in contact with a middle portion between the front end of the separation membrane toward the inlets and the rear end of the separation membrane toward the discharge zone.

4. The microfluidic chip according to claim 1, wherein the separation holes are from 100 nm to 1000 nm in diameter.

5. The microfluidic chip according to claim 1, wherein the separation membrane is produced by sequentially forming a silicon nitride film and a silicon oxide film on the surface of a substrate.

6. The microfluidic chip according to claim 1, wherein a silicon oxide film is formed on the surface of the separation holes.

7. The microfluidic chip according to claim 1, further comprising a magnetic force application unit provided between the reaction zone and the separation zone of the fluidic channel.

8. The microfluidic chip according to claim 7, further comprising an outlet disposed between the magnetic force application unit and the separation zone to discharge unreacted samples therethrough.

9. A method for detecting a biological substance using the microfluidic chip according to claim 1, the method comprising 1) introducing samples and a fluid into the fluidic channel of the microfluidic chip, 2) allowing the samples to react in the reaction zone to produce reaction products, 3) detecting the reaction products not passing through the separation holes present in the separation zone of the fluidic channel, and 4) analyzing the detected reaction products.

10. The method according to claim 9, wherein magnetic nanoparticles, a biological substance, and a probe are introduced as the samples in step 1) and the samples are allowed to react to form magnetic nanoparticles-biological substance-probe complexes in step 2).

11. The method according to claim 10, wherein a receptor bound to the magnetic nanoparticles and a receptor bound to the probe recognize the biological substance to form the magnetic nanoparticles-biological substance-probe complexes.

12. The method according to claim 9, further comprising fixing and collecting unreacted magnetic nanoparticles and the magnetic nanoparticles-biological substance-probe complexes by a magnetic force application unit between steps 2) and 3).

13. The method according to claim 12, further comprising discharging unreacted samples unfixed by the magnetic force application unit through an outlet after the fixing/collection step.

14. The method according to claim 13, wherein after discharge of the unreacted samples, the application of the magnetic force by the magnetic force application unit is stopped to allow the unreacted magnetic nanoparticles and the magnetic nanoparticles-biological substance-probe complexes to move in the direction from the inlets of the fluidic channel toward the discharge zone.

15. The method according to claim 9, wherein after movement of the unreacted magnetic nanoparticles and the magnetic nanoparticles-biological substance-probe complexes toward the discharge zone, the unreacted magnetic nanoparticles pass through the separation holes but the magnetic nanoparticles-biological substance-probe complexes do not pass through the separation holes.

16. A method for producing a separation membrane including separation holes for the microfluidic chip according to claim 1, the method comprising 1) forming a silicon nitride film on a silicon substrate or a substrate comprising silicon by chemical vapor deposition (CVD), 2) forming 2 to 3 μm diameter separation holes in the substrate, and 3) forming a silicon oxide film on the substrate comprising the separation holes by chemical vapor deposition (CVD).

17. The method according to claim 16, wherein, in step 3), the chemical vapor deposition (CVD) is continued until the diameter of the separation holes is reduced to a range of 100 nm to 1000 nm.

18. A method for detecting a biological substance using the microfluidic chip, wherein the microfluidic chip comprises a sample inlet, a fluid inlet, and a fluidic channel wherein the fluidic channel consists of a reaction zone, a separation zone, and a discharge zone sequentially disposed in the downstream direction and the separation zone comprises a separation membrane formed with one or more separation holes through which nanoparticles pass, the method comprising
    1) introducing samples and a fluid into the fluidic channel of the microfluidic chip;
    2) allowing the samples to react in the reaction zone to produce reaction products,
        2-i) fixing and collecting unreacted magnetic nanoparticles and the magnetic nanoparticles-biological substance-probe complexes by a magnetic force application unit
        2-ii) discharging unreacted samples unfixed by the magnetic force application unit through an outlet after the fixing/collection step;
    3) detecting the reaction products not passing through the separation holes present in the separation zone of the fluidic channel; and
    4) analyzing the detected reaction products,
    wherein after discharge of the unreacted samples, the application of the magnetic force by the magnetic force application unit is stopped to allow the unreacted magnetic nanoparticles and the magnetic nanoparticles-biological substance-probe complexes to move in the direction from the inlets of the fluidic channel toward the discharge zone.

19. The method according to claim 18, wherein magnetic nanoparticles, a biological substance, and a probe are introduced as the samples in step 1) and the samples are allowed to react to form magnetic nanoparticles-biological substance-probe complexes in step 2).

20. The method according to claim 19, wherein a receptor bound to the magnetic nanoparticles and a receptor bound to the probe recognize the biological substance to form the magnetic nanoparticles-biological substance-probe complexes.

* * * * *